United States Patent [19]

Schnurr et al.

[11] Patent Number: 5,508,465

[45] Date of Patent: Apr. 16, 1996

[54] PREPARATION OF ALIPHATIC ALPHA, OMEGA-AMINONITRILES IN THE GAS PHASE

[75] Inventors: Werner Schnurr, Herxheim; Joachim Wulff-Döring, Frankenthal; Rolf Fischer, Heidelberg; Rudolf Bäzner, Mannheim, all of Germany

[73] Assignee: BASF Aktiengesellschaft, Ludwigshafen, Germany

[21] Appl. No.: 373,420

[22] Filed: Jan. 17, 1995

[30] Foreign Application Priority Data

Jan. 3, 1995 [DE] Germany ............ 195 00 040.4

[51] Int. Cl.$^6$ .............................. C07C 253/30
[52] U.S. Cl. ................................... 558/459
[58] Field of Search ............................ 558/459

[56] References Cited

U.S. PATENT DOCUMENTS

| | | | |
|---|---|---|---|
| 2,257,814 | 10/1941 | Rigby | 558/459 |
| 3,174,992 | 3/1965 | McCracken | 558/459 |
| 4,362,671 | 12/1982 | Diamond et al. | 558/459 |
| 4,389,348 | 6/1983 | Diamond et al. | 558/459 |
| 4,601,859 | 7/1986 | Galle et al. | 558/459 |
| 5,151,543 | 9/1992 | Ziemecki | 558/459 |

FOREIGN PATENT DOCUMENTS

| | | | |
|---|---|---|---|
| 0161419 | 11/1985 | European Pat. Off. | 558/459 |
| 534939 | 3/1941 | United Kingdom | 558/459 |

OTHER PUBLICATIONS

Medina, et. al., J. Chem. Soc. Faraday Trans. (1993), vol. 89, No. 21, pp. 3981–3986.

Fierro, et. al., J. of Molecular Catalysis, vol. 61, (1990), pp. 197–205.

*Primary Examiner*—Joseph Paul Brust
*Attorney, Agent, or Firm*—Keil & Weinkauf

[57] ABSTRACT

Aliphatic alpha,omega-aminonitriles are prepared by partial hydrogenation of aliphatic alpha,omega-dinitriles at elevated temperatures in the presence of a catalyst in the gas phase by a process which comprises carrying out the hydrogenation with a catalyst based on at least one metal selected from the group consisting of nickel, cobalt, ruthenium and rhodium and with the proviso that the catalyst is not a powder.

9 Claims, No Drawings

PREPARATION OF ALIPHATIC ALPHA, OMEGA-AMINONITRILES IN THE GAS PHASE

The present invention relates to an improved process for the preparation of aliphatic alpha,omega-aminonitriles by partial hydrogenation of aliphatic alpha,omega-dinitriles at elevated temperatures in the presence of a catalyst in the gas phase.

J. Mol. Cat. 61 (1990), 197–205 describes the gas-phase hydrogenation of adiponitrile over iron and nickel catalysts doped with alkali metal, in the absence of ammonia. Furthermore, J. Chem. Soc. Faraday Trans. 89 (1993), 3981–3986 describes the partial hydrogenation of adiponitrile over catalysts which contain 30% by weight of nickel and are doped with potassium. At reaction temperatures of 170° C. and atmospheric pressure, yields of up to 85% are obtained at a conversion of 65%. However, the disadvantage of these methods is that the catalysts are in powder form and therefore unsuitable for large-scale industrial realization in a fixed bed, particularly because of the short catalyst life. Furthermore, a large excess of hydrogen is used, and the catalyst space velocity of 0.02 kg of dinitrile per 1 of catalyst per hour is also useless for commercial use.

It is an object of the present invention to provide an improved process for the preparation of aliphatic alpha, omega-aminonitriles by partial hydrogenation of adiponitrile, which does not have the abovementioned disadvantages. In particular, it was intended to find a catalyst which has a longer life than the catalysts used to date.

We have found that this object is achieved by a process for the preparation of aliphatic alpha,omega-aminonitriles by partial hydrogenation of aliphatic alpha,omega-dinitriles at elevated temperatures in the presence of a catalyst in the gas phase by carrying out the hydrogenation with a catalyst based on at least one metal selected from the group consisting of nickel, cobalt, ruthenium and rhodium and with the proviso that the catalyst is not a powder.

Aliphatic alpha,omega-dinitriles of the general formula I

   I where n is an integer from 1 to 10, in particular 2, 3, 4, 5 or 6, are used as starting materials in the novel process. Particularly preferred compounds I are succinonitrile, glutaronitrile, adiponitrile, pimelonitrile and suberonitrile, very particularly preferably adiponitrile.

In the novel process, the dinitriles I described above are partially hydrogenated in the presence of a catalyst to give alpha,omega-aminonitriles of the general formula II

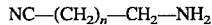   II where n has the abovementioned meanings. Particularly preferred aminonitriles II are those in which n is 2, 3, 4, 5 or 6, in particular 4, ie. 4-aminobutyronitrile, 5-aminopentanenitrile, 6-aminohexanenitrile (6-aminocapronitrile), 7-aminoheptanenitrile and 8-aminooctanenitrile, very particularly preferably 6-aminocapronitrile.

The reaction is carried out as a rule at from 100° to 250° C., preferably from 150° to 220° C., particularly preferably from 160° to 200° C.; the pressure is chosen in general in the range from 0.01 to 3, preferably from 0.07 to 1, particularly preferably from 0.09 to 0.5, MPa.

The hydrogen concentration in the inlet gas depends essentially on the dinitrile concentration. Usually, the molar ratio of hydrogen to dinitrile is chosen in the range from 2:1 to 300:1, preferably from 10:1 to 200:1.

In a preferred embodiment, ammonia or an amine, particularly preferably ammonia, is additionally used. Particularly when ammonia is used, observations to date have shown that the catalyst life is increased. The amount of ammonia or amine is usually from 5 to 50, preferably from 10 to 30 % by weight, based on dinitrile used.

According to the invention, the catalysts used are those based on at least one metal selected from the group consisting of nickel, cobalt, ruthenium and rhodium, preferably those based on nickel.

The catalysts may be used in the form of unsupported or supported catalysts, suitable carriers being, for example, alumina, silica, aluminosilicates, titanium dioxide, zirconium dioxide, and magnesium oxide, preferably alumina, silica and aluminosilicates, particularly preferably alumina.

In a preferred embodiment, the catalysts may be modified with a modifier based on a metal selected from the group consisting of lithium, sodium, potassium, rubidium, caesium, magnesium, calcium, strontium, barium, scandium, yttrium, lanthanides, silver, cadmium, aluminum, tin and zinc, preferably with the oxides thereof. Alkali metal oxides, such as lithium oxide, sodium oxide, potassium oxide, rubidium oxide and caesium oxide, and zinc oxide are particularly preferred, caesium oxide being very particularly preferred.

The amount of catalyst is chosen in general so that the catalyst space velocity is from 0.03 to 10, preferably from 0.05 to 3, kg of dinitrile per kg of catalyst per hour.

When supported catalysts are used, the metal content of the catalyst is usually chosen in the range from 0.1 to 80, preferably from 0.2 to 70, particularly preferably from 0.5 to 50, % by weight, based on the carrier.

According to the invention, the catalysts are not used in the form of powder but as moldings, such as extrudates, pellets and beads, depending on the intended use.

The reaction is preferably carried out continuously as fixed-bed reaction using a fixed catalyst, for example by the liquid-phase or trickle-bed procedure. By changing the residence time, the conversion and hence the selectivity can be controlled.

The preparation of the catalysts is known per se (cf. Appl. Het. Cat., (1987), 106–122; Catalysis 4 (1981), 1–30; DE-A 2 260 978). The preparation is usually carried out by precipitating water-soluble salts, such as nitrates, sulfates, chlorides, formates or acetates, of the corresponding metals in the presence or absence of a carrier, if desired processing the resulting catalyst precursor to give extrudates or pellets, drying the product and then calcining it. Supported catalysts are in general also obtainable by impregnating the carrier with an aqueous salt of the corresponding metal or of the corresponding metals, if desired in the presence of the abovementioned modifiers, in particular caesium compounds, or by spraying the corresponding metal salt solutions onto the carrier.

The precipitation is effected in general either by adding precipitating reagents or by changing the pH or the temperature.

The preliminary catalyst material thus obtained is usually dried, in general at from 80° to 150° C., preferably from 80° to 120° C.

The calcination is effected, as a rule, at from 150° to 700° C., preferably from 200° to 650° C., in a gas mixture comprising hydrogen and nitrogen.

In the novel process, the catalysts used, in particular supported catalysts, exhibit high activity over a longer period than in the past. Alpha,omega-aminonitriles are obtained in high yield and with good selectivities. The alpha,omega-aminonitriles are important starting compounds for the preparation of cyclic lactams, in particular 6-aminocapronitrile for caprolactam.

EXAMPLES

EXAMPLE 1

67 ml of an aqueous nickel/nitrate solution (nickel content 16.72 g, calculated as nickel metal) were added to 225 g of alumina extrudates (diameter 4 mm, BET surface area 1 $m^2/g$) and the mixture was left to stand for two hours at room temperature with repeated, thorough stirring. The resulting catalyst precursor was then dried for 16 hours at 120° C. and calcined for 4 hours at 350° C. The total process was then repeated.

After cooling, the extrudates were placed in a reduction apparatus and flushed for 2 hours with 20 l of nitrogen per hour. Thereafter, the extrudates were heated to 300° C. at 2° C./min and while passing in 20 l of hydrogen per hour and were kept at this temperature for 20 hours. After cooling in a stream of nitrogen, the catalyst was passivated with an air/nitrogen mixture, the temperature increasing not more than 20° C.

The catalyst extrudates obtained contained 13% by weight of nickel (calculated as metal and based on alumina).

EXAMPLE 2

Example 1 was repeated, except that impregnation with lithium nitrate (32 ml of 3.4% strength by weight solution) was carried out before the impregnation with nickel nitrate.

The catalyst extrudates obtained contained 13% by weight of nickel and 0.1% by weight of lithium, the percentage in each case being calculated as metal and based on alumina.

EXAMPLE 3

Example 1 was repeated, except that impregnation with sodium nitrate (32 ml of a 1.4% strength by weight solution) was carried out before the impregnation with nickel nitrate.

The catalyst extrudates obtained contained 13% by weight of nickel and 0.1% by weight of sodium, the percentage in each case being calculated as metal and based on alumina.

EXAMPLE 4

Example 1 was repeated, except that impregnation with potassium nitrate (32 ml of a 1.0% strength by weight solution) was carried out before the impregnation with nickel nitrate.

The catalyst extrudates obtained contained 13% by weight of nickel and 0.1% by weight of potassium, the percentage in each case being calculated as metal and based on alumina.

EXAMPLE 5

Example 1 was repeated, except that impregnation with caesium nitrate (32 ml of a 0.5% strength by weight solution) was carried out before the impregnation with nickel nitrate.

The catalyst extrudates obtained contained 13% by weight of nickel and 0.1% by weight of caesium, the percentage in each case being calculated as metal and based on alumina.

EXAMPLE 6

Example 5 was repeated with an alumina which had a BET surface area of 5.5 $m^2/g$ (SCS 9 (Pechiney)).

The catalyst extrudates obtained contained 13% by weight of nickel and 0.1% by weight of caesium, the percentage in each case being calculated as metal and based on alumina.

EXAMPLE 7

Example 5 was repeated with an alumina which had a BET surface area of 7.7 $m^2/g$ (SPH 512 B (Rhone-Poulenc)).

The catalyst extrudates obtained contained 13% by weight of nickel and 0.1% by weight of caesium, the percentage in each case being calculated as metal and based on alumina.

EXAMPLE 8

From 3 to 20 g of adiponitrile per hour were passed into an evaporator (300° C.) and from there, with from 100 to 200 l/h of hydrogen, over 100 ml of catalyst by the trickle-bed procedure. The gaseous reacted mixture was condensed in cold traps and analyzed by gas chromatography. Further reaction parameters and the results are shown in the table below.

TABLE

| Catalyst from: | | Temperature [°C.] | $H_2$/ADN-Molar ratio | Catalyst space velocity [g of ADN per g of cat. × h] | ACN-yield [%] | HMD-yield [%] | ACN-selectivity [%] | Conversion [%] |
|---|---|---|---|---|---|---|---|---|
| Example 1 | a | 180 | 60 | 0.07 | 54 | 4 | 75 | 72 |
|  | b | 200 | 60 | 0.07 | 56 | 13 | 59 | 95 |
| Example 2 |  | 180 | 45 | 0.08 | 22 | 0.3 | 85 | 26 |
| Example 3 |  | 180 | 45 | 0.08 | 5 | 0 | 71 | 7 |
| Example 4 |  | 180 | 45 | 0.08 | 16 | 0.2 | 89 | 18 |
| Example 5 | a | 180 | 45 | 0.08 | 49 | 1 | 88 | 56 |
|  | b | 200 | 45 | 0.08 | 60 | 4 | 79 | 76 |
| Example 6 | a | 180 | 45 | 0.1 | 25 | 0.5 | 89 | 28 |
|  | b | 180 | 60 | 0.1 | 21 | 0.3 | 91 | 23 |
|  | c | 200 | 45 | 0.1 | 29 | 0.4 | 85 | 34 |
|  | d | 180 | 150 | 0.05 | 46.4 | 1.4 | 92 | 50.7 |
|  | a | 180 | 45 | 0.1 | 71 | 3 | 91 | 78 |
|  | b | 180 | 90 | 0.1 | 54 | 2 | 93 | 58 |
|  | c | 180 | 50 | 0.2 | 34 | 1 | 92 | 37 |
|  | d | 180 | 60 | 0.2 | 28 | 0.5 | 93 | 30 |

We claim:

1. A process for the preparation of aliphatic alpha,omega-aminonitriles of the formula II $$NC\text{---}(CH_2)_n\text{---}CH_2\text{---}NH_2 \qquad \text{II}$$

where n is an integer from 1 to 10, by partial hydrogenation of aliphatic alpha,omega-dinitriles of the formula I $$NC\text{---}(CH_2)_n\text{---}CN \qquad \text{I}$$

where n has the abovementioned meanings, in the gas phase at a temperature in the range of from 100° to 250° C. and at a pressure in the range of from 0.01 to 3 MPa, whereby the molar ratio of hydrogen to dinitrile I is chosen in the range of from 2:1 to 300:1, which process comprises: carrying out the reaction in a fixed-bed reactor using a fixed-bed catalst, the fixed-bed catalyst being at least one metal selected from the group consisting of nickel, cobalt, ruthenium and rhodium, and wherein the amount of catalyst is chosen so that the catalyst space velocity is from 0.03 to 10 kg of dinitrile I per kg of catalyst per hour.

2. The process of claim 1, wherein the catalyst is modified with at least one metal selected from the group consisting of lithium, sodium, potassium, rubidium, caesium, magnesium, calcium, strontium, barium, scandium, yttrium, lanthanides, silver, cadmium, aluminum, tin and zinc.

3. The process of claim 1, wherein the hydrogenation is carried out at from 150° to 250° C.

4. The process of claim 1, wherein the hydrogenation is carried out at from 0.07 to 1 MPa.

5. The process of claim 1, wherein adiponitrile is used as the aliphatic alpha,omega-dinitrile and 6-aminocapronitrile is obtained.

6. The process of claim 1, wherein the fixed-bed catalyst is a nickel catalyst.

7. The process of claim 1, wherein the fixed-bed catalyst is a nickel catalyst which is modified with caesium oxide.

8. The process of claim 1, wherein the fixed-bed catalyst is an alumina supported catalyst.

9. The process of claim 1, wherein the fixed-bed catalyst is in the form of an extrudate, pellet or bead.

* * * * *